(12) United States Patent
Reisner et al.

(10) Patent No.: US 6,368,572 B1
(45) Date of Patent: Apr. 9, 2002

(54) USE OF HEMATOPOIETIC DEFICIENT CELL TRANSPLANTED CHIMERIC NONHUMAN MAMMALS AS HUMAN BACTERIAL TOXIN SHOCK MODELS

(75) Inventors: Yair Reisner, Tel-Aviv (IL); George Lowell, Baltimore, MD (US); Esther Aboud-Pirak, Kiryat Tivon (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 08/452,492

(22) Filed: May 30, 1995

Related U.S. Application Data

(63) Continuation of application No. 08/015,021, filed on Feb. 5, 1993, now abandoned.

(51) Int. Cl.$^7$ ......................... A61K 49/00; C12N 15/00
(52) U.S. Cl. ............................. 424/9.1; 424/9.2; 800/2
(58) Field of Search ................................. 424/9.2, 93.7, 424/577; 800/2, DIG. 5

(56) References Cited

FOREIGN PATENT DOCUMENTS

| EP | 0469632 | 2/1991 |
| EP | 0517199 | 12/1992 |
| WO | 9304168 | 3/1993 |

OTHER PUBLICATIONS

Morrison, Bacterial Endotoxins and Pathogenesis, *Reviews of Infectious Diseases* 5:S733–S747 (1983).

McCune, et al., The SCID–hu Mouse: Murine Model for the Analysis of Human Hematolymphoid Differentiation and Function, *Science* 241:1632–1639 (1988).

Bosma, et al., A severe combined immunodeficiency mutation in the mouse, *Nature*, 301:527–530 (1983).

Roth, et al., Altered hepatic vasopressin and $\alpha_1$–adrenergic receptors after chronic endotoxin infusion, *Rapid Communications*, E699–E702 (1987).

Moore, et al., Influence of Endotoxin on Graft–versus–Host Disease After Bone Marrow Transplantation Across Major Histocompatibility Barriers in Mice, *Transplantation* 43:731–736 (1986).

Geraci, et al., Hepatic Injury after Whole–Liver Irradiation in the Rat, *Radiation Research* 101:508–518 1985.

Evans, et al., Differential Expression of Interleukin–1 and Tumore Necrosis Factor in Murine Septic Shock Models, *Circulatory Shock* 29:279–290 (1989).

Yelich, Glucoregulatory, Hormonal, and Metabolic Responses to Endotoxicosis or Cecal Ligation and Puncture Sepsis in the Rat: A Direct Comparison, *Circulator Shock* 31:351–363 (1990).

Parrillo, et al. Septic Shock in Humans—Advances in the Understanding of Pathogenesis, Cardiovascular Dysfunction, and Therapy, *Anals of Internal Medicine* 113:227–241 (1990).

Zuckerman, et al., Regulation of Serum Tumor Necrosis Factor in Glucocorticoid–Sensitive and –Resistant Rodent Endotoxin Shock Models, *Infection and Immunity* 57:3009–3013 (1989).

Miethke et al., T Cell–mediated Lethal Shock Triggered in Mice by the Superantigen Staphylococcal Enterotoxin B: Critical Role of Tumor Necrosis Factor, Journal of Experimental Medicine, vol. 175, pp. 91–98, Jan. 1992.

*Primary Examiner*—Brian R. Stanton
(74) *Attorney, Agent, or Firm*—Browdy and Neimark

(57) ABSTRACT

A chimeric non-human mammal M3 having its hematopoietic cells substantially destroyed and replaced by hematopoietic cells from a hematopoietic deficient mammal, wherein M3 is susceptible to bacterial toxin-related pathologies found in humans, and to methods of making and using thereof.

12 Claims, 2 Drawing Sheets

FIGURE 2

USE OF HEMATOPOIETIC DEFICIENT CELL TRANSPLANTED CHIMERIC NONHUMAN MAMMALS AS HUMAN BACTERIAL TOXIN SHOCK MODELS

This application is a continuation of application Ser. No. 08/015,021, filed Feb. 5, 1993, now abandoned in favor of the present application.

BACKGROUND OF THE INVENTION

1. Field of the Invention

The present invention relates to the field of immunology and animal models, and, more particularly, to non-human chimeric mammals, where hematopoietic cells have been replaced by hematopoietic cells received from donor mammals having a hematopoietic deficiency, and to methods for their production, wherein such chimeric animals may be used as animal models of bacterial toxin shock.

2. Description of the Background Art

Bacteria produce endotoxins and exotoxins which are known to cause toxin related pathologies, such as toxic shock in humans, which can result in death. Exotoxins are usually heat-labile proteins of great toxicity, typically formed by gram-positive bacteria, e.g. of the genera *Micrococcus, Staphylococcus, Streptococcus, Corynebacterium, Lactobacillus, Bacillus* and *Clostridium*. The endotoxins are usually heat-stable lipopolysaccharide-protein complexes of high toxicity, typically formed by gram-negative bacteria, e.g., of the genera *Brucella, Haemophilus, Escherichia, Klebsiella, Proteus, Salmonella, Pseudomonas, Shigella, Vibrio, Yersinia,* etc. *Staphylococcus aureus,* in particular, produces an exotoxin designated Staphylococcal enterotoxin B (SEB), that has been associated with toxic shock syndrome (TSS), a syndrome characterized by high fever, vomiting, diarrhea, confusion, and skin rash that may rapidly progress to severe and intractable shock. Septic shock, a disease with significant morbidity and with overall mortality from 50 to 90%, is associated with bacteremia due to gram-negative bacteria or meningococci.

Research in the bacterial shock field has historically been hindered by the absence of relevant and cost-effective animals models. Laboratory animals, including severe combined immune deficient (SCID) mice and other mutant mice, are highly insensitive to bacterial toxins. Models in other animals, including primates, are being developed but have not become widely used. Sensitivity to bacterial toxins was found to be increased in mice by inducing liver toxicity with i.p. injections of D-galactosamine (Galanos et al., Proc. Natl. Acad. Sci. U.S.A. 76:5939 (1979); Lehmann et al., J. Exp. Med. 165:657 (1987)).

The mode of action of bacterial exotoxins is unclear as yet. Some of these toxins exhibit the unusual properties of superantigens, and are able to bind to human and mouse major class II histocompatibility antigens and the complex formed can stimulate a large number of T cells, expressing appropriate Vβ segments of the T cell receptor (TCR). It is likely that this ability to induce a massive T cell proliferation is related, at least in part, to the pathological effects of the toxins, since it was shown that T cell-derived lymphokines appear to cause shock-like syndromes and that T cell repopulation of SCID mice conferred sensitivity to Staphylococcal enterotoxin B (SEB). However, because mice are more resistant than humans to the pathogenic effects of bacterial toxins, the latter experiment was performed in a mouse model in which liver metabolism was impaired by i.p. injection of D-galactosamine (Miethke et al., J. Exp. Med. 175:91–98 (1992)). Although this D-galactosamine sensitized mouse model provides some increase in sensitivity to SEB, the other physiological effects of D-galactosamine may be expected to make such a mouse model unsuitable as the response is not shown to directly mimic the physiological effects found in human SEB shock.

Wood et al., FEMS Microbiology Immunology 76: 121–134 (1991), disclose that in animal models, humans and primates react similarly to staphylococcus enterotoxins (SEs) and, for this reason, the monkey has been used to study the effects of SE's following either oral or intravenous administration. However, primates are not the ideal model and it has proved difficult to find a suitable alternative. Dwarf goats and rabbits are susceptible to SE's, but neither is appropriate for large-scale studies. Rodents are relatively unreactive, being capable of surviving large doses of toxin.

The lack of similar response in animal models, such as mice or other rodents, has hindered the development of a suitable model of human bacterial toxin related pathologies. Accordingly, there is a need to provide chimeric non-human mammals for use as animal models for human bacterial toxin shock by providing animal models that respond similarly to humans in terms of symptomology, pathology and therapeutic response.

EP 469,632, published Feb. 5, 1992, by McCune et al. and assigned to SyStemix, Inc., discloses the determination of the response of a pathogen (other than retroviruses, such as bacteria) tropic to a particular species, to a stimulus by (1) administration of a stimulus, able to induce a physiological response from tissue cells of the particular species, to an immunocompromised host, other than a primate, lacking at least functional T cells; and (2) determining the effect of the stimulus, wherein the tissue cells are vascularized, non-transformed solid organ tissue. Also SCID/hu mice (having human transplanted tissue) are disclosed which are infected in the human tissue with a pathogen tropic for this tissue. The solid tissue is a hematopoietic tissue, and the host is a SCID/SCID mouse (having autosomal recessive mutation SCID). The SCID/hu mice can be used to evaluate the effect of drugs and vaccines, and of agents (or conditions) on specific tissues or on the immune system. The human tissue is disclosed to remain viable for more than four weeks.

Bosma et al. (Nature 301:527–530(1983)) describe and characterize an immunodeficient mouse as an autosomal recessive trait wherein differentiation of both B and T lymphocytes is impaired. To determine whether the particular C.B.-17 scid mice had a defective cellular environment for lymphoid differentiation, reciprocal bone marrow transfers were made between the SCID C.B.-17 scid mice and BALB/c mice. However, while the bone marrow from the BALB/c mice donors to SCID recipients showed the BALB/c bone marrow cell allotype, none of the SCID donor bone marrow allotype was found after transplant into BALB/c recipient. Accordingly, SCID bone marrow was not shown to survive in sublethally irradiated BALB/c mice, due to replacement by the BALB/c irradiated bone marrow cells, such that transplant of SCID bone marrow into BALB/c mice is disclosed to be unsuccessful.

The use of T cell-deficient SCID mice as bone marrow cell donors in an allogeneic bone marrow transplantation model in which the recipient mice have destroyed bone marrow, resulted in markedly enhanced rejection compared to syngeneic control grafts (Murphy et al., J. Immunol. 144:3305–3331 (1990)). Accordingly, this reference discloses the unsuitability and lack of successful transplant of bone marrow cells into allogeneic or xenogeneic recipients having a destroyed immune system.

Citation of documents herein is not intended as an admission that any of the documents cited herein is pertinent prior art, or an admission that the cited documents are considered material to the patentability of the claims of the present application. All statements as to the date or representation as to the contents of these documents is based on the information available to the applicant and does not constitute any admission as to the correctness of the dates or contents of these documents.

SUMMARY OF THE INVENTION

It is an object of the present invention to overcome one or more deficiencies of the related art.

For production of a useful non-human mammal model of human bacterial toxin pathologies according to the present invention, it has unexpectedly been discovered that non-human mammals, preferably rodents, normally resistant to bacterial toxins, are made susceptible to bacterial toxin pathologies present in humans, when their hematopoietic cells have been substantially destroyed and replaced by hematopoietic cells from non-human mammals having a hematopoietic deficiency. In a preferred embodiment, the recipient mammal is a mouse, more preferably mouse strain C3H/HeJ.

Thus, according to the present invention, an animal model for human bacterial toxin pathologies is provided by using a normal or other suitable non-human mammal M1, wherein the hematopoietic cells of the mammal M1 are substantially destroyed and replaced by hematopoietic cells derived from a non-human mammal M2 having a hematopoietic deficiency, to provide a chimeric non-human mammal M3, which is unexpectedly found to provide a non-human mammal model of human bacterial toxin-related pathologies.

The present invention is thus directed, in one aspect, to a non-human chimeric mammal M3 having long-term stable donor-type hematopoietic cells, comprising a mammal M1, the hematopoietic cells of which have been substantially suppressed or destroyed and replaced by hematopoietic cells originating from a mammal M2 having a hematopoietic deficiency, which mammal M3 is susceptible to bacterial toxin-related pathologies found in humans.

According to the present invention, any non-human mammal with a hematopoietic deficiency may be used as the donor, M2. The hematopoietic deficiency of M2 may be selected from severe combined immunodeficiency (SCID), an erythroid cell deficiency, a myeloid cell deficiency, a T cell deficiency, a B cell deficiency or any other hematopoietic deficiency. Useful mouse strains with hematopoietic deficiencies include immunodeficient SCID, Bg/Nu/Xid (BNX), Nu mice or erythroid deficient W/W$^V$ mice, or any combination thereof. Gene-deleted hematopoietic deficient mammals are also intended within the scope of the present invention as M2 donors.

The mammal donor M2 is of a species the same or other than the mammal recipient M1. Preferably, M1 and is M2 belong to the same rodent genus or species In preferred embodiments, M2 is a SCID mouse and M1 is a C3H/HeJ mouse.

The source of hematopoietic cells of a hematopoietic deficient mammal M2 used according to the present invention may be selected or derived from:

(a) unfractionated or fractionated bone marrow cells;
(b) unfractionated or fractionated blood cells;
(c) unfractionated or fractionated spleen or thymus cells;
(d) unfractionated or fractionated cord blood cells;
(e) unfractionated or fractionated fetal tissue (liver, thymus, bone marrow, spleen or blood); and
(f) any combination thereof.

The cells may be used directly, as cell cultures and/or after being passaged one or more times in vitro or in vivo, such as 2, 3, 4, 5 or more times.

The present invention also provides a method for the production of a non-human chimeric mammal M3, comprising:

a) treating a non-human mammal M1 so as to substantially destroy the immune system of M1; and
b) transplanting the treated mammal M1 with hematopoietic cells originating from a mammal M2 having a hematopoietic deficiency;

thereby obtaining a chimeric non-human mammal M3 having hematopoietic cells derived from mammal donor M2, wherein M3 is susceptible to bacterial toxin shock or other bacterial toxin-related pathological conditions such as those found in humans.

The non-human chimeric M3 mammals of the present invention can be used as animal models to test and evaluate drugs and/or diagnostic agents for human pathologic conditions involving bacterial toxins, wherein the mammal M3 responds to bacteria or at least one toxin as administered as an intramuscular, intravenous or subcutaneous injection, or via ingestion, aerosol, inhalation, or other respiratory, topical or gastrointestinal introduction or by exposure to the bacterial toxin or bacteria in a similar physiological manner as humans may be exposed The invention also comprises a method for evaluating a human bacterial toxin pathology in a non-human animal model, comprising:

a) administering to a non-human chimeric mammal M3 as described herein with a bacterial toxin; and
b) evaluating the physiological response of administered mammal M3, as a model of human bacterial toxin shock.

The invention further comprises a method for evaluating potential therapeutic agents for the treatment of human bacterial toxin shock in a non-human animal model, comprising:

a) administering to a non-human chimeric mammal M3 as described herein with a bacterial toxin;
b) administering said therapeutic agent in a therapeutically effective amount to said chimeric mammal M3; and c) evaluating the physiological response of administered mammal M3, as a model of human bacterial toxic shock to determine the effectiveness of said therapeutic agent in treating or preventing the pathological effects of exposure to said bacterial toxin, wherein steps (a) and (b) can be performed concurrently, (a) before (b) or (b) before (a).

DESCRIPTION OF THE FIGURES

FIG. 2 is a graphical representation showing dose response for SEB-mediated toxic shock in SCID:C3H/HeJ chimera. Different doses of SEB were administered i.v. to SCID:C3H/H3J chimera 42 days post-BMT.

DETAILED DESCRIPTION OF THE PREFERRED EMBODIMENTS

According to the present invention, hematopoietic deficient, such as immunodeficient, non-human mammals M2 are used as hematopoietic cell donors to mammals M1, after causing the hematopoietic cells of the mammal M1 to be substantially destroyed, such that one or more hematopoietic lineages reconstituted in the resulting chimera M3 are deficient, resulting in susceptibility to bacterial toxin-related pathologies present in humans. Such a discovery is unexpected, since mice do not respond to toxin exposure or administration as humans.

Thus, according to the present invention, non-human mammals having their hematopoietic cells substantially destroyed and replaced by hematopoietic cells from a hematopoietic deficient non-human mammal are discovered to respond to bacterial toxin exposure or administration in a similar manner as do humans.

The non-human recipient mammal, M1, of the present invention may be any mammal, but preferably it is a rodent, such as, for example, mouse, rabbit, hamster, guinea pig, rat, etc. M1 may be a normal mammal, a transgenic mammal, a mutated strain or a gene-deleted mammal as is known in the art. An example of a gene-deleted mammal is a mouse lacking the β2-macroglobulin gene, which is unable to express major histocompatibility antigens (mouse H-2 antigens) on the cell surface. However, H-2 compatibility is not required. In some cases, the non-human mammal recipient M1 may also be an animal with a hematopoietic deficiency that can be irradiated before transplantation of bone marrow from mammal donor M2, thus providing as recipient an animal likely to be more immunosuppressed than currently available hematopoietic deficient strains of mice. Preferably, M1 is a normal mouse, most preferably a mouse of strain C3H/HeJ.

The source of hematopoietic cells from mammal M2 is preferably T cell-depleted bone marrow. Both allogeneic and syngeneic transplants are encompassed by the invention.

In a preferred embodiment of the invention, a chimeric mouse M3, having long term stable hematopoietic cells derived from a SCID mouse M2, is produced by a method comprising (a) treating a recipient mouse M1 so as to substantially destroy its immune system; and (b) transplanting the treated mouse M1 with T cell-depleted SCID mouse bone marrow cells, thereby obtaining a chimeric mouse M3 susceptible to bacterial toxin shock or other bacterial toxin-related pathologies found in humans. Preferably the mouse M1 is from strain C3H/HeJ or any mouse having a normal immune system, such as a BALB/c mouse.

In all of the embodiments of the present invention, it is important that the hematopoietic cells of the animal being treated, be substantially destroyed. It is understood, however, that it is often inevitable that some hematopoietic cells survive the treatment and this will not affect the processes of the present invention. As long as the number of hematopoietic cells which survive are insufficient to protect the animal from the lethal effect of conditioning in the absence of the transplant from mammal M2, then the cells are considered to be "substantially destroyed". The term "substantially destroyed" is not intended to comprehend a sublethal treatment, such as a sub-lethal dose of radiation. Thus, those of ordinary skill in the art in the relevant arts will understand that the term "substantially destroy" means to leave such a small number of surviving cells that the animal could not survive under normal laboratory conditions.

Such dosages may be selected from cumulative dosages of 400 to 5000 RADs, or any value or range therein, which is sufficient to substantially destroy the hematopoietic cells and tissues of a mammal M1. Non-limiting examples of irradiation dosages to substantially destroy the hematopoietic system of a mammal M1 include more than 1000–1100 RADs (10–11 Gy) for H3H/HeJ and BALB/c mice.

As discussed above, it is known from previous studies of murine bone marrow transplantation (for review, see: van Bekkum, D. W. et al. (1985) *Bone Marrow Transplantation: Biological Mechanisms and Clinical Practice,* Dekker, N.Y.) that, following lethal doses of total body irradiation, some host hematopoietic cells survive the conditioning protocols. Other hematopoietic cells can be generated by surviving early progenitor cells, which have retained their ability to differentiate and proliferate despite the massive doses of radium or chemotherapy. Since the present invention comprehends the possibility of a relatively small number of such host-type lymphocytes or other hematopoietic cells remaining after destruction, they will occasionally be found in the chimeric mammals of the present invention.

In the method of the invention for the production of the chimeric mammal M3, the treatment in step (a) for suppression or destruction of the hematopoietic system of mammal M1 may include irradiation (e.g., X-ray or gamma irradiation), chemotherapy, or a combination of both, or cytoreduction with specific monoclonal or polyclonal antibodies directed against M1 hematopoietic cells.

The chimeric non-human mammal M3 of the present invention can be used as an animal model which enables test of vaccines, prophylactic agents or modalities, therapeutic agents and/or diagnostic agents for human bacterial toxin-related pathologies or diseases.

The vaccine or prophylactic agent to be tested in an animal model of the invention may be selected from but is not limited to a toxoid, toxin-fragment, peptide, lipid, saccharide, or covalent or hydrophobic conjugate of any of these that is used to produce active or passive antibody, cell-mediated, or cytokine-mediated protection against bacterial toxin or cytokine-related pathologies or diseases. The present invention can also be used to identify toxic fragments of toxins and test for safety and efficacy of putative toxoids or vaccine candidates. Any therapeutic agent which has the potential to be effective for treating a human bacterial toxin-related pathology can be tested and evaluated in the animal model of the present invention. Such agents may be selected from, but are not limited to, known and new compounds and compositions including antibiotics, steroids, cytotoxic agents, vasoactive drugs, antibodies and other therapeutic modalities. Non-limiting examples of such agents include antibiotics used in the treatment of bacterial shock, such as gentamicin, tobramycin, nafcillin, parenteral cephalosporins, etc; adrenal corticosteroids and analogs thereof, such as methyl prednisolone, that mitigate the cellular injury caused by endotoxins; vasoactive drugs, such as alpha-receptor blocking agents (e.g., phenoxybenzamine), beta-receptor agonists (e.g., isoproterenol), and dopamine, that are agents that are suitable for treating septic shock. Such types of therapeutic agents can be tested and evaluated in animal models of the present invention for the potential treatment of bacterial toxin-related pathologies, without undue experimentation, based on the teaching and guidance presented herein. In addition, any other drug or modality suggested in future treatment or prophylaxis of bacterial shock or sepsis may be tested using animal models of the present invention.

Figure 1:
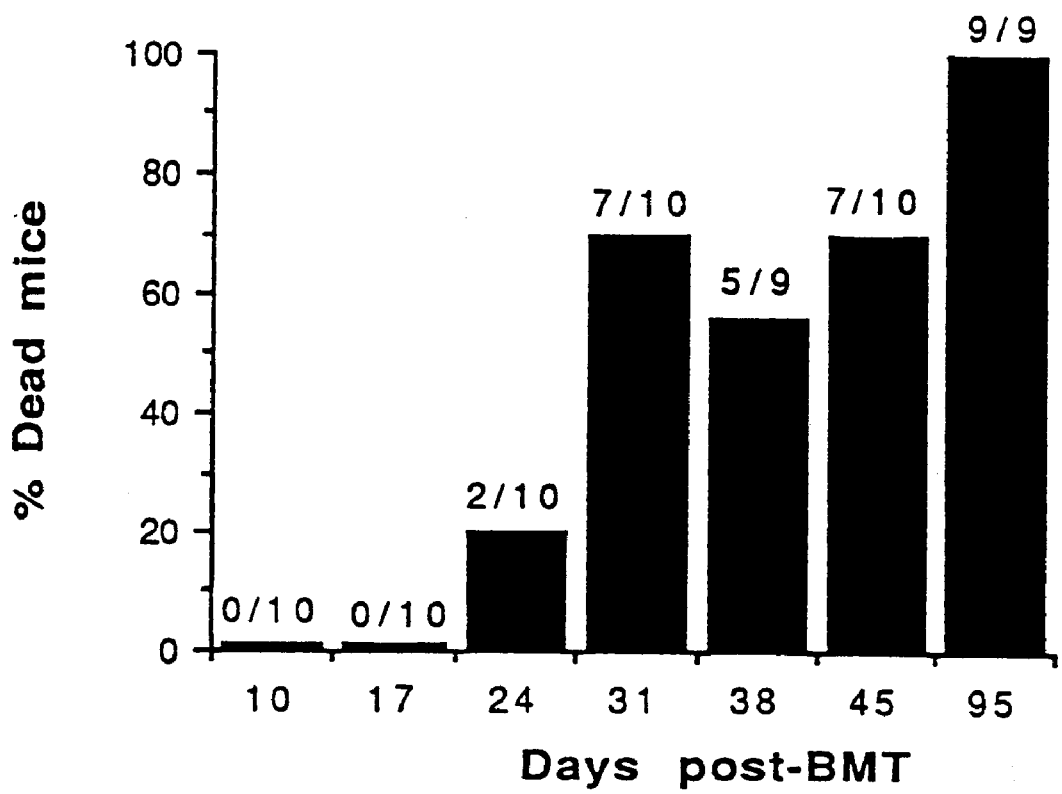
FIG. 1 is a graphical representation showing the kinetics of toxic shock induction in SCID:C3H/HeJ chimera. Nine week C3H/HeJ female mice were irradiated with 11 Gy total body irradiation (TBI) and transplanted with T cell-depleted SCID bone marrow ($1\times10^6$ cells). At different days post-bone marrow transplant (BMT), mice were given 10 $\mu$g SEB i.v. and the percentage of mortality was recorded.

Diagnostic agents can also be tested and evaluated using animal models of the present invention, such as those capable of detecting the presence of a toxin or toxin-producing bacteria in the animal model. These diagnostic agents may preferably be labeled to facilitate detection, e.g., with enzymatic, radioactive, fluorescent, chemiluminescent or bioluminescent labels.

The present invention thus provides the ability to test any vaccine or any prophylactic, therapeutic and/or diagnostic agent to prevent, treat or diagnose human bacterial toxin-related pathologies or diseases.

As used herein bacterial toxin includes both endotoxins and exotoxins produced by any naturally occurring, mutant or recombinant bacteria which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), *Staphylococcal* enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), Staphylococcus species (e.g., *Staphylococcus aureus, Staphylococcus pyogenes*), Shigella species (e.g., *Shigella dysenteriae, Shigella flexneri, Shigella boydii,* and *Shigella sonnei*), Salmonella species (e.g., *Salmonella typhi, Salmonella cholera-suis, Salmonella enteritidis*), Clostridium species (e.g., *Clostridium perfringens, Clostridium dificile,* *Clostridium botulinum*), Camphlobacter species (e.g., *Camphlobacter jejuni, Camphlobacter fetus*), Heliobacter species, (e.g., *Heliobacter pylori*), Aeromonas species (e.g., *Aeromonas sobria, Aeromonas hydrophila, Aeromonas caviae*), Pleisomonas shigelloides, Yersina enterocolitica, Vibrios species (e.g., *Vibrios cholerae, Vibrios parahemolyticus*), Klebsiella species, Pseudomonas aeruginosa, and Streptococci. Such strains can produce toxins which cause pathologies and symptoms in humans and other animals, such as toxic shock, food poisoning, toxic shock syndrome, systemic shock, emesis, gastroenteritis, enterocolitis, diarrhea, fever, hypotension, dehydration, lung congestion and collapse, abdominal distension, mucosal hemorrhage, intestinal and smooth muscle inflammation, leukocytosis, septicemia, hepatitis, neuromuscular poisoning, cramps, vomiting, nausea, and related symptoms. See, e.g., Stein, ed., INTERNAL MEDICINE, 3rd ed., pp 1–13, Little, Brown and Co., Boston, (1990); Evans et al., eds., Bacterial Infections of Humans: Epidemiology and Control, 2d. Ed., pp 239–254, Plenum Medical Book Co., New York (1991); Mandell et al, Principles and Practice of Infectious Diseases, 3d. Ed., Churchill Livingstone, N.Y. (1990); Berkow et al, eds., The Merck Manual, 16th edition, Merck and Co., Rahway, N.J., 1992; Wood et al, FEMS Microbiology Immunology, 76:121–134 (1991); Marrack et al, Science, 248:705–711 (1990), the contents of which references are incorporated entirely herein by reference.

A non-limiting example is based on Staphylococcal enterotoxin B (SEB), with lethality as the endpoint. In this model, the hematopoietic cells of the non-human mammal M1, such as a mouse, e.g. C3H/HeJ or BALB/c mouse, are substantially destroyed, and are then reconstituted with hematopoietic cells from a hematopoietic deficient non-human mammal M2 of the same or similar species, such as a mouse, e.g. a SCID, BNX or Nu mouse or the like. After recovery from the transplantation procedures, the resulting chimeric mice have been unexpectedly discovered to be sensitive to bacterial toxins, such as SEB, in a similar manner to humans.

A chimeric non-human mammal used according to the present invention responds to, presents symptoms of, and/or provides macroscopic and microscopic pathological conditions of bacteria or bacterial toxin exposure, in a highly similar manner as do humans. Thus, a chimeric non-human mammal of the present invention is expected to provide superior animal models for human bacterial toxin shock exposure, administration or infection, for in vivo testing of new therapeutic or diagnostic agents or modalities.

Having now generally described the invention, the same will be more readily understood through reference to the following examples which are provided by way of illustration, and are not intended to be limiting of the present invention, unless specified.

EXAMPLE 1

Transplantation of SCID Bone Marrow into Lethally Irradiated C3H/HeJ Mice

Eight to 12 week-old female C3H/HeJ mice were exposed to a single dose of 10-11 Gy TBI from a gamma beam 150-A $^{60}Co$ source (produced by the Atomic Energy of Canada, Kanata, Ontario) with a focal skin distance (F.S.D.) of 75 cm, at a 0.7 Gy/min dose rate. One day later, T cell-depleted bone marrow from 8- to 12-week-old male SCID mice (Weizmann Institute Animal Breeding Center) was prepared according to Reisner et al., (1978) Proc. Natl. Acad. Sci. USA 75, 2933), with minor modifications (Schwartz, E. et al., (1987) J. Immunol. 138:460), and $0.5-1.0 \times 10^6$ cells were transplanted per mouse.

The resulting mice survived at least three months and provide suitable animal models for human bacterial toxin pathologies, beginning 4 weeks after bone marrow transplantation. Four weeks after transplantation, 9 animals were challenged with 10 μg SEB given intravenously and 5 died over the subsequent 72 hrs resulting in 56% lethality. Nine control mice given buffered saline were entirely healthy.

In another experiment, lethally irradiated C3H/HeJ mice were transplanted with $1 \times 10^6$ SCID bone marrow cells per animal and challenged 25 days later with 10 μg SEB (iv), as presented above. In this experiment, 5 of 7 (71%) of animals challenged with SEB died while 8 of 8 similarly transplanted control animals given buffered saline remained entirely healthy.

This experiment was repeated with the exception that, as shown in FIG. 1 and described in the description of FIG. 1, mice received 11 Gy and were transplanted with $1 \times 10^6$ bone marrow cells. At different days post-transplantation, mice were challenged with 10 μg SEB (iv) and, as shown in FIG. 1, from 31–45 days lethality ranged from 56% to 70% and 100% lethality was attained by challenging 12 weeks post-transplantation. Control mice receiving only saline were healthy.

Figure 2:
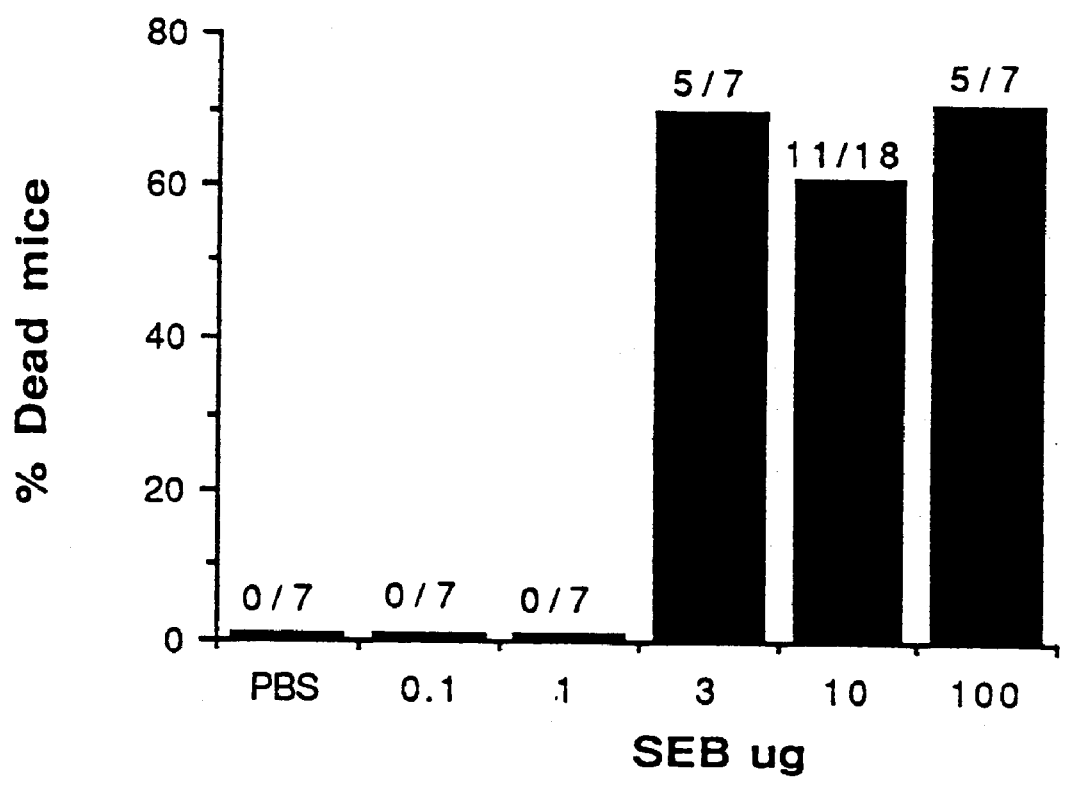

In another experiment, shown in FIG. 2, C3H/HeJ mice were irradiated and transplanted with T cell depleted SCID bone marrow cells as described above subject to the following modifications. Forty-two days after transplant, animals were given a single intravenous injection of SEB at 0.1, 1.0, 3.0, 10 or 100 μg, or phosphate-buffered saline (PBS) as a control. No deaths were observed in animals receiving PBS, or SEB at 0.1 or 1.0 μg; 61–71% mortality was seen in the three highest SEB dose groups.

EXAMPLE 2

Transplantation of SCID Bone Marrow into Lethally Irradiated BALB/c Mice

Mice were treated as noted above such that, BALB/c mice were irradiated with 10 Gy, transplanted with 1×$10^6$ SCID bone marrow cells per animal and challenged with 10 μg SEB (iv) 4 weeks later whereupon 1 of 3 animals (33%) challenged with SEB died. In another experiment using 3 groups of BALB/c mice as recipients, 9 mice per group (total 27 mice) challenged either 5, 7 or 9 weeks post-transplantation suffered 33%, 44% and 22% lethality, respectively. Similarly transplanted control animals given buffered saline remained entirely healthy. These results indicate that BALB/c mice can also serve as recipients in this model.

Macroscopic and microscopic examination of animals that died of SEB challenge were consistent with death due to exotoxin shock including pulmonary and gastrointestinal vascular congestion and leukocytosis.

EXAMPLE 3

Comparisons of Transplant of Hematopoietic Deficient and Normal Bone Marrow into Irradiated C3H/H3J Mice for Toxin Sensitivity The following example was performed as in Example 1, except as otherwise indicated. Eight to 12 week old female C3H/HeJ mice were irradiated as in Example 1, with 10.5 Gy at a rate of 0.68 Gy/min and bone marrow from SCID (1×$10^6$ or 0.5×$10^6$ cells) and BALB/c mice (0.5×$10^6$ cells) was transplanted. After 25 days, the mice were treated i.v. with 10 μg SEB.

As shown in Table I, toxin shock sensitivity can be induced only in irradiated mice that received bone marrow transplant from hematopoietic deficient mice, thus resulting in a reconstituted immune system that is deficient. Administration of SCID bone marrow together with BALB/c bone marrow results in normal lymphoid reconstitution and does not produce SEB-sensitive mice.

TABLE I

Effect of SEB, administered 25 days after bone marrow transplantation, on C3H mice

| Bone marrow transplant | Treatment | Number of mice | Number of Deaths |
|---|---|---|---|
| 1 × $10^6$ SCID | SEB | 7 | 5 |
| 1 × $10^6$ SCID | PBS | 8 | 0 |
| 0.5 $10^6$ SCID + 0.5 $10^6$ BALB/c | SEB | 9 | 0 |

All references cited herein are entirely incorporated by reference herein, including all data, tables, figures, cited references and text presented in the cited references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention.

What is claimed is:

1. A method for evaluating a bacterial exotoxin pathology in a mouse model, comprising:

(a) providing a chimeric mouse M3 comprising a mouse M1 which is resistant to bacterial exotoxins, wherein said mouse M1 has been (i) treated to substantially destroy the hematopoietic cells of the mouse M1 such that the resulting treated M1 mouse could not survive under normal laboratory conditions, and then (ii) transplanted with hematopoietic cells from a mouse M2 having a severe combined immunodeficiency, thereby forming said chimeric mouse M3;

(b) administering to said chimeric mouse M3 at least one bacterial exotoxin; and then (c) evaluating the physiological response of the toxin administered to said mouse M3 as a model of a bacterial exotoxin pathology.

2. A method according to claim 1, wherein said mouse M2 is a SCID mouse and said mouse M1 is a C3H/HeJ mouse or a BALB/c mouse.

3. A method according to claim 1, wherein said bacterial exotoxin pathology is caused by an exterotoxin produced by at least one strain of bacteria selected from the group consisting of a strain of an enterotoxigenic *E. coli* species, a *Staphylococcus Species*, a *Salmonella species*, a *Clostridium species*, a *Campylobacter species*, a *Heliobacterium species*, an *Aeromonas species*, *Yersinia enterocolitica*, a *Vibrio species* and a *Klebsiella species*.

4. A method according to claim 1, wherein said bacterial exotoxin is *Staphylococcus* enterotoxin B.

5. A method for evaluating potential therapeutic agents or modalities for the treatment or prophylaxis of a bacterial exotoxin pathology in a mouse model, comprising:

(a) administering to a chimeric mouse M3 a bacterial exotoxin;

(b) administering a predetermined amount of said therapeutic agent to said chimeric mouse M3; and (c) evaluating the physiological response of administered mouse M3, as a model of said bacteria-related human pathology, to determine the effectiveness of said potential therapeutic agent in treating or preventing the pathological effects of exposure to said bacterial exotoxin;

wherein said mouse M3 comprises a mouse M1 which is resistant to bacterial exotoxins, the hematopoietic cells of which have been substantially destroyed and replaced by hematopoietic cells derived from a mouse M2 having a severe combined immunodeficiency.

6. A method according to claim 5, wherein steps (a) and (b) are performed concurrently.

7. A method according to claim 5, wherein steps (a) and (b) are performed (a) before (b).

8. A method according to claim 5, wherein steps (a) and (b) are performed (b) before (a).

9. A method according to claim 5, wherein said mouse M2 is a SCID mouse.

10. A method according to claim 9, wherein said mouse M1 is a C3H/eJ mouse or a BALB/c mouse.

11. A method according to claim 5, wherein said bacteria-related pathology is caused by an enterotoxin produced by at least one bacteria selected from the group consisting of a strain of an enterotoxigenic *E coli* species, a *Staphylococcus species*, a *Salmonella species*, a *Clostridiuum species*, a *Campylobacter species*, a *Heliobacterium species*, an *Aeromonas species*, *Yersinia enterocolitica*, a *Vibrio species*, and a *Klebsiella species*.

12. A method according to claim 5, wherein said bacterial exotoxin is *Staphylococcus enterotoxin B*.

* * * * *